(12) United States Patent
Wendelken et al.

(10) Patent No.: US 7,029,446 B2
(45) Date of Patent: Apr. 18, 2006

(54) STANDOFF HOLDER AND STANDOFF PAD FOR ULTRASOUND PROBE

(76) Inventors: Martin Edmund Wendelken, 610 Boulevard, Elmwood Park, NJ (US) 07407; Charles Pope, 199 Donald Rd., Guliford, NJ (US) 06437

( * ) Notice: Subject to any disclaimer, the term of this patent is extended or adjusted under 35 U.S.C. 154(b) by 0 days.

(21) Appl. No.: 10/695,988

(22) Filed: Oct. 30, 2003

(65) Prior Publication Data

US 2005/0096547 A1   May 5, 2005

(51) Int. Cl.
  *A61B 8/14*   (2006.01)
(52) U.S. Cl. ...................................... 600/459
(58) Field of Classification Search ........ 600/437–472; 128/916
  See application file for complete search history.

(56) References Cited

U.S. PATENT DOCUMENTS

| | | | | |
|---|---|---|---|---|
| 4,722,346 A | * | 2/1988 | Chen | 600/459 |
| 4,796,632 A | * | 1/1989 | Boyd et al. | 600/459 |
| 4,815,470 A | * | 3/1989 | Curtis et al. | 600/459 |
| 5,050,436 A | * | 9/1991 | Kunii et al. | 73/644 |
| 5,078,149 A | | 1/1992 | Katsumata et al. | |
| 5,135,001 A | * | 8/1992 | Sinofsky et al. | 600/459 |
| 5,265,614 A | | 11/1993 | Haykawa et al. | |
| 5,381,795 A | * | 1/1995 | Nordgren et al. | 600/472 |
| 5,782,767 A | | 7/1998 | Pretlow | |
| 5,830,144 A | * | 11/1998 | Vesely | 600/459 |
| 6,132,378 A | * | 10/2000 | Marino | 600/459 |
| 6,139,502 A | * | 10/2000 | Fredriksen | 600/459 |
| 6,638,767 B1 | * | 10/2003 | Unger et al. | 435/458 |

FOREIGN PATENT DOCUMENTS

EP           0527651 A1 *   2/1993

\* cited by examiner

*Primary Examiner*—Ali Imam

(57) ABSTRACT

An accommodative standoff holder 10 which can be used for both diagnostic and therapeutic ultrasound is disclosed. The described standoff holder 10 has the ability to be mounted on and utilized with transducers 20 of different sizes and shapes. The standoff holder 10 includes a gel insert 26 which is removable and self adjusting assuring contact between a human body, an animal, or other object and the acoustic window 22 of a transducer 22.

7 Claims, 5 Drawing Sheets

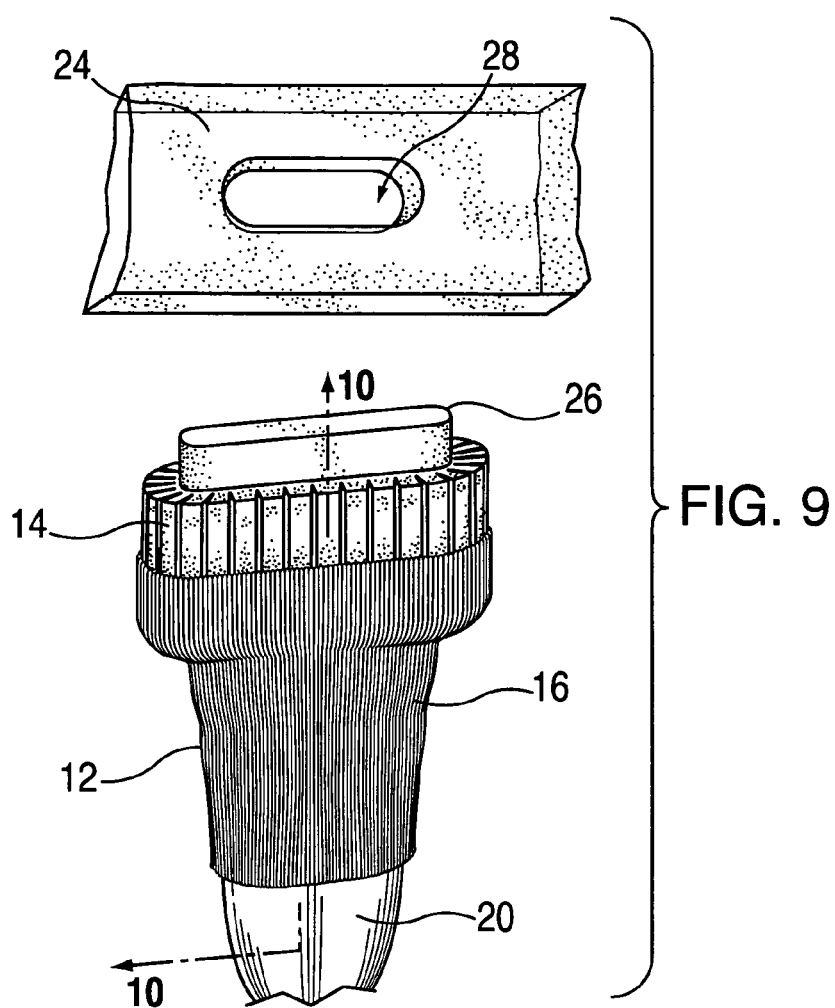
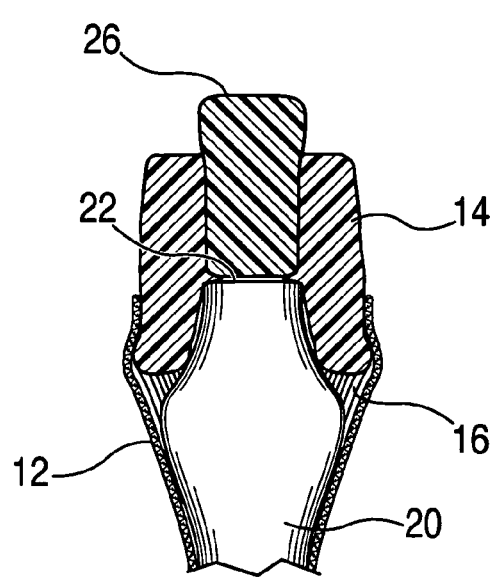

STANDOFF HOLDER AND STANDOFF PAD FOR ULTRASOUND PROBE

FIELD OF THE INVENTION

The field of the invention relates to a temporary holder of a standoff pad for an ultrasound probe utilized during a diagnostic ultrasound exam or therapeutic ultrasound treatment.

BRIEF DESCRIPTION OF PRIOR ART AND BACKGROUND OF THE INVENTION

Diagnostic ultrasound is a medical procedure used to image both humans and animals in order to obtain images of a body. Images are taken of different organs or body systems and have been broken down into approximately 20 application areas as defined by the United States Food and Drug Administration (FDA). Some examples of the clinical applications are diagnostic ultrasound of musculoskeletal system, peripheral vascular system, and abdominal ultrasound. Therapeutic ultrasound is a medical treatment modality that is use to treat various abnormal conditions. The intent of this modality is to provide relief and cure the abnormal condition. An example therapeutic ultrasound would be to treat some inflammation of an injured or inflamed tendon that courses around the ankle. Both methods employ a probe which emits ultrasound waves into a body usually through a contact media. Coupling gel is an example of contact media which is placed between the probe surface and skin surface of a body.

A standoff pad is another type of contact media used to couple an ultrasound probe to a body which will be receiving either therapeutic or diagnostic ultrasound waves. A standoff pad provides a clinician with a number of advantages by incorporating its use during an ultrasound exam or treatment. In diagnostic ultrasound, a standoff pad will shift or move the images being observed during an ultrasound exam, deeper into the field on the ultrasound monitor. For example, if the standoff pad is 1 centimeter thick, a 1 centimeter space is created between ultrasound probe and the skin surface. The image displaced on the ultrasound monitor is equal to the thickness of the standoff pad. All images observed on the ultrasound screen will show this 1 centimeter space while using the standoff pad. An advantage of moving the image away from the top of a monitor is that it allows a clinician to analyze superficial structures including the skin surface during a superficial musculoskeletal examination.

Another use of a standoff pad is to insure coupling between an ultrasound transducer (probe) and a body receiving ultrasound waves. Standoff pads are usually made of a soft compliant material such as a gel pad. A gel pad has the ability to conform to a hard noncompliant surface such as the ankle bone on the foot. Without a standoff pad the ridged surface of a probe touching the rigid bony ankle causes gaping or spaces between the transducer and the ankle. Such gaping yields artifacts and poor image quality during a diagnostic ultrasound exam. At the same time, gaping reduces the healing benefits in therapeutic ultrasound due to poor contact. Therapeutic ultrasound waves can not enter the body without solid contact.

Standoff pads also provide an additional benefit to those receiving treatment or being imaged using ultrasound. The pad serves as a soft interface between the hard probe surface and the body thereby reducing discomfort produced by pressure on an area.

There are a number of different types of standoff pads available for use during ultrasound exams. The methods used to couple the ultrasound probe to the standoff pad vary with the particular standoff used. Some standoff pads are incorporated and attached to a cover or holder which is placed over the end of a probe. One such example is disclosed in U.S. Pat. No. 6,132,378 (2000) Marino; who describes a probe cover that incorporates on its end, two membrane sheets sealed causing a cavity to be formed. The cavity can be filled with a substance such as water or oil to allow for the transmission of ultrasound waves. The membrane is pliable and allows for compliance during its use. Marino describes rigid covers which must be specifically designed for each type of probe. Any space between the membrane and the probe surface will cause a lack of contact to occur and a failure to transmit ultrasound waves. The probe cover that Marino describes clearly has the membranes permanently fixed to the end of the cover. This means that the membrane interface itself can not move and therefore does allow for possibility of poor compliance using this cover. Further, Marino teaches about a collar (or ridge) on the transducer for the probe cover to snap on to. Unfortunately not all ultrasound probes have collars as described. This feature does pose inherent contact issues because the Marino described probe covers will not be able to snap onto the some transducers (probes). An incorrect fit along with a fixed membrane will lead to poor contact with the surface of the probe. Another standoff adaptor is described in U.S. Pat. No. 4,796,632 (1998) Boyd, et al; involves the attachment of a molded coupler portion and a second compression molded receptacle portion to a probe. The two housings are combined and the first housing is filled with a fluid which allows the ultrasound waves to be conveyed from the probe to a body. The fluid filled housing serves as a standoff allowing for imaging in the near field. This standoff adaptor is rather complex in that-it involves a two chamber device that is specifically made for a particular type of transducer shape. Further once attached to a transducer, the adapter must be filled with a fluid to insure ultrasound wave to be transmitted through the adaptors second chamber. This adaptor has inherent problems as it is described that can cause poor imaging and ultrasound waves not to be transmitted. Some examples are improper filling of the chamber, gases or bubbles in the fluid within the chamber, and leaking fluid due to improper seals within the chamber. Still another coupling pad is described in U.S. Pat. No. 5,782,767 (1998) Pretlow; which consists of an assembly of layers that includes a thin gel pad, foam pad, and a polypropylene net which allows ultrasound waves to be transmitted into a body. Although the embodiment of the assembly serves as a coupling medium for ultrasound waves, it lacks the ability to serve as a standoff pad which shifts an image into the far field, one of the main attributes of a using a standoff pad. Other acoustic coupling devices are described in U.S. Pat. No. 5,265,614 (1993) Hayakawa, et al.; and U.S. Pat. No. 5,078,149 (1992) Katsumata, et al; both describe standoff that have been molded for specific probes made of poly vinyl alcohol or other water containing polymetric gels. Although these acoustic couplers provide an acoustical pathway for ultrasound waves, they are not intended to be disposable. Such ultrasonic couplers are expensive to produce because each probe involves the production of a mold to be made before the standoff is produced. There are disposable gel standoff pads commercially available which can be purchased for ultrasound imaging. One example is Aquaflex® ultrasound gel pad manufactured by Parker Laboratories, INC (Fairfield, N.J., USA). This company provides a 2 cm×9 cm aqueous, bacteriostatic round disposable which can be used as a coupler by a ultrasound probe. These discs shaped standoffs are placed on the body and allow for ultrasound waves to be transmitted and received by a transducer. A problem with using this standoff pad is that the operator of the ultrasound device needs to use two hands; one hand to hold the transducer, the other to hold the standoff pad. Using both hands presents the sonographer with the difficulty of making adjustments to dials or controls on an ultrasound unit while performing an exam or treatment. Another less obvious issue about the above stated standoff covers or assembles is that none allow for a variety of pad thickness. In some ultrasound applications one may require thin standoff pads while other ultrasound applications require thick standoff pads. Also, if a sonographer would like to change materials incorporated into such contact devices, it involves the fabrication of another assembly or cover. Sill another problem with present molded or adaptor type standoff is the generation of artifacts within the ultrasound images. These artifacts are caused by the aging and fatigue of the materials that make up the standoff pad itself which, are fixed to the above stated adaptors.

Although these methods are novel for their intended purposes all of the above described ultrasound couplers fail to provide a single coupling device that has all of the following properties.

An ultrasound coupling pad that is intended to be disposable.

An ultrasound coupling device that has a pad which is not molded or fixed to its holder.

An ultrasound coupling device which uses a coupling pad that can be temporally fixed to transducers.

An ultrasound coupling device that can accommodate various shapes and sizes of transducers.

An ultrasound coupling device that allows for a gel pad that has variable thickness.

An ultrasound coupling device that allows the operator to change the type of a gel pad being use anytime.

An ultrasound coupling device which allows the operator of the ultrasound scanner to scan use one hand feeing the second hand to make adjustments to the controls on the ultrasound machine.

An ultrasound coupling device that provides for free vertical movement of a gel pad within the standoff hold.

The present invention discloses and provides a standoff holder that satisfies all of the above properties using one device. This novel invention is a standoff holder that is flexible and self adjusting. The device has the ability to be used by a variety of ultrasound transducer (probes) regardless of shape. If the transducer is round, oval, or has a square terminal emitting surface, the disclosed standoff holder will accommodate the probe shape. Most ultrasound scanners are FDA approved for more than one clinical application and therefore use different probes for each of the different applications. A standoff holder that can accommodate the different shapes and sizes will reduce the number of contact devices and therefore the overall costs of ultrasound coupling devices. The disclosed standoff holder accommodates a gel standoff pad that is not permanently fixed to the holder. This property allows for the use of an inexpensive gel pad that is disposable. New gel pads also insure a clear, artifact free path for ultrasound waves to travel into tissues. A gel pad that can move and self adjusted within the standoff holder provides better contact between the acoustic window on the probe surface and the gel pad itself This novel standoff holder may also accommodate a variety of pad thickness. A sonographer has the option of choosing a standoff gel pad that is appropriate for a given application. Finally, the present standoff holder disclosed only requires the sonographer to use one hand freeing the second to make adjustments to the scanner controls.

OBJECTIVES AND ADVANTAGES

The disclosed standoff holder fulfills the imaging capability and therapeutic treatment needs of a health care practitioner using an ultrasound transducer. After mounting the described standoff holder over the body of an ultrasound probe numerous advantages become apparent over previous disclosed devices.

A principal objective is to provide a single standoff holder that can be used by a variety ultrasound transducer of different shapes and sizes.

Another objective of this standoff holder is to allow for the use of disposable standoff pads.

Still another objective of this standoff holder is to provide an examiner with the ability to utilize the standoff holder with gel pad using one hand.

Another objective is to allow a practitioner to use this standoff holder on both diagnostic ultrasound and therapeutic ultrasound transducers.

Still another objective of this standoff holder is to allow the use of gel pads which may be of different thickness.

A further objective of this standoff holder is to allow the use of one standoff holder for a number of ultrasound applications.

Yet another objective of this standoff holder is to reduce the risk of transmittable diseases by using a disposable gel pad.

Another objective of this standoff holder is to lower the overall costs of an ultrasound coupling device.

Still another objective is to have an adjustable and freely movable gel pad which is not fixed to the standoff holder.

Another objective is to improve contact between the gel pad and the acoustic window of a transducer.

Yet another objective of using this standoff holder is to reduce image artifacts and material breakdown.

These objectives and advantages will become apparent with the following description and clarified with referral to drawings provided.

BRIEF DESCRIPTION OF DRAWINGS

FIG. 9 is a drawing of a transducer with the standoff holder placed over the body of the transducer with a gel insert placed within.

FIG. 10 is another view of the standoff holder, gel insert, and transducer taken at lines 10—10 in FIG. 9.

Figure 1:
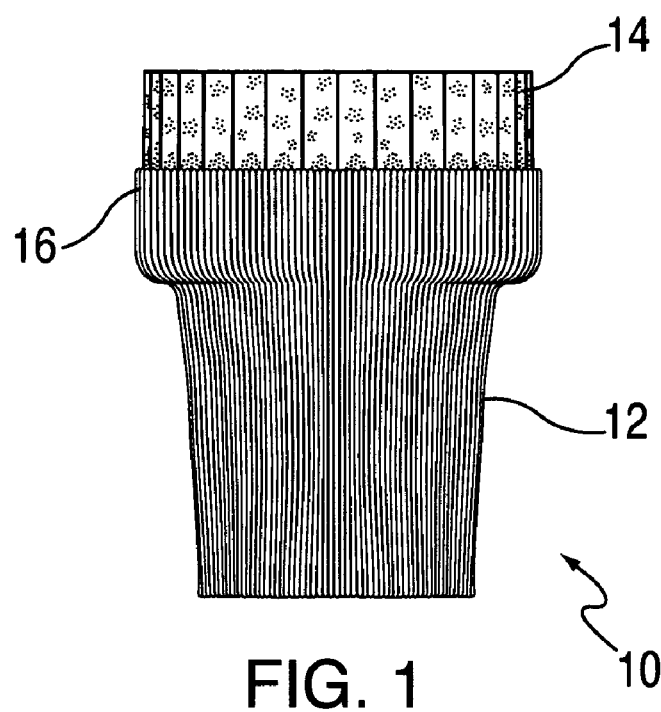
FIG. 1 is an overall view of a standoff holder.

| Reference Numerals in Drawings | |
|---|---|
| 10 multi-ribbed standoff holder | |
| 12 elastic sock of standoff holder | 14 expansion collar of standoff holder |
| 16 expansion rib | 18 opening in collar of standoff holder |
| 20 body of transducer | 22 acoustic window of transducer |
| 24 gel pad | 26 gel insert |
| 28 void in gel pad | 30 elastic collar |

DESCRIPTION OF EMBODIMENT—FIG. 1 TO 13

Referring to FIG. 1, a drawing of multi-ribbed standoff holder 10. Multi-ribbed standoff holder 10 is preferably based on sock 12 which is made of a soft pliable material such as an elastic cloth or rubber sock. Elastic sock 12 when stretched or expanded has memory which will cause it contract and to return to its normal shape when such tension is released. Elastic sock 12 on one end is comprised of solely elastic material and allows for great flexibility with little to no rigidity. As one travels along elastic sock 12 toward its opposite end, elastic sock 12 begins to loose flexibility and increases in rigidity. At the opposite end of elastic sock 12 an expansion collar 14 is comprised of a number of strips of rigid material such as plastic which are incorporated into elastic sock 12. Between these strips of plastic which make up expansion collar 14 areas of plain elastic sock exist providing and forming a number of expansion ribs 16. An expansion rib 16 is found between the alternating strips of plastic that comprise collar 14 found on the distal end of elastic sock 12.

Figure 2:
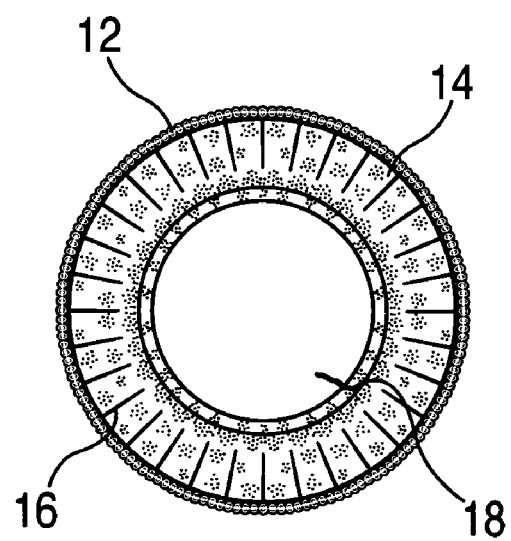
FIG. 2 is a view of a standoff holder looking into the open end or mouth.

In FIG. 2, multi-ribbed standoff holder 10 is viewed looking into opening 18 found within expansion collar 14 on the distal end. In FIG. 2 also note that expansion ribs 16 found between the strips of expansion collar's 14 ridged material appear close. FIG. 2 illustrates the multi-ribbed standoff holder 10 before it is mounted or stretched over the external surface of a transducer 20.

Figure 3:
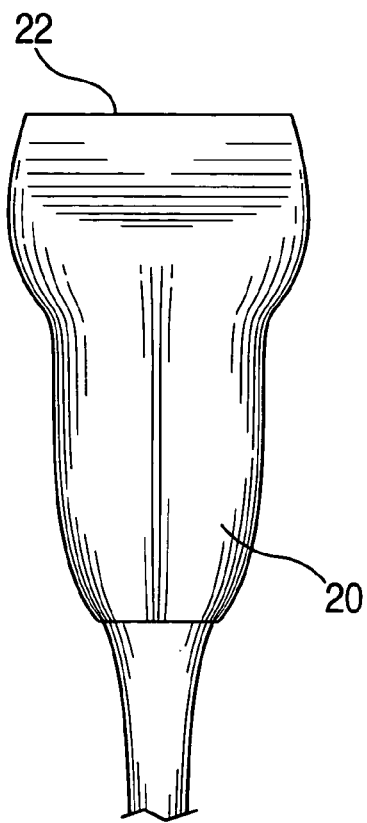
FIG. 3 is a drawing of a typical ultrasound transducer.
Figure 4:
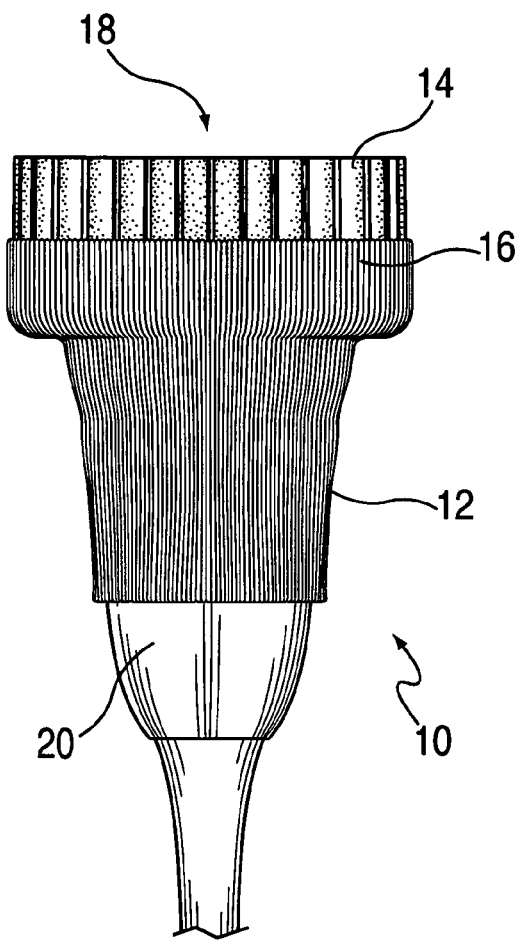
FIG. 4 is the standoff holder placed over the body of a transducer.

Directing ones attention to FIG. 3, a picture of a typical ultrasound transducer 20. Ultrasound transducer 20 has a terminal surface where the ultrasound waves are emitted and subsequent echo are captured know as an acoustic window 22. FIG. 4 is an image of ultrasound transducer 20 having multi-ribbed standoff holder 10 mounted over the exterior surface. In FIG. 4 note that expansion ribs 16 appear open due to the fact that multi-ribbed standoff holder 10 has been mounted over the external surface of transducer 20.

Figure 5:
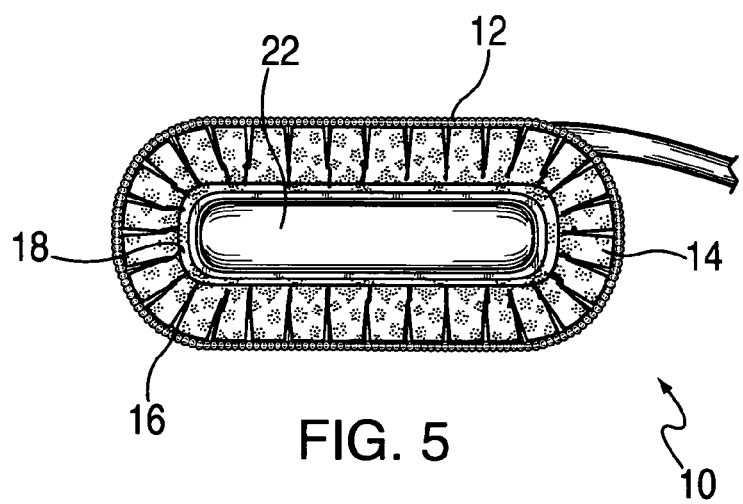
FIG. 5 is view of the standoff holder fitted over a transducer looking into the opening of the standoff holder.

FIG. 5 is a view of the multi-ribbed standoff holder 10 placed over the exterior surface of transducer 20 looking into its distal end. Note that within the expansion collar 14, opening 18 allows full access of acoustic window 22 located on the distal end of ultrasound transducer 20. Also note that expansion ribs 16 within expansion collar 14 are stretched open while multi-ribbed standoff holder 10 is place over the outer surface of ultrasound transducer 20.

Figure 6:
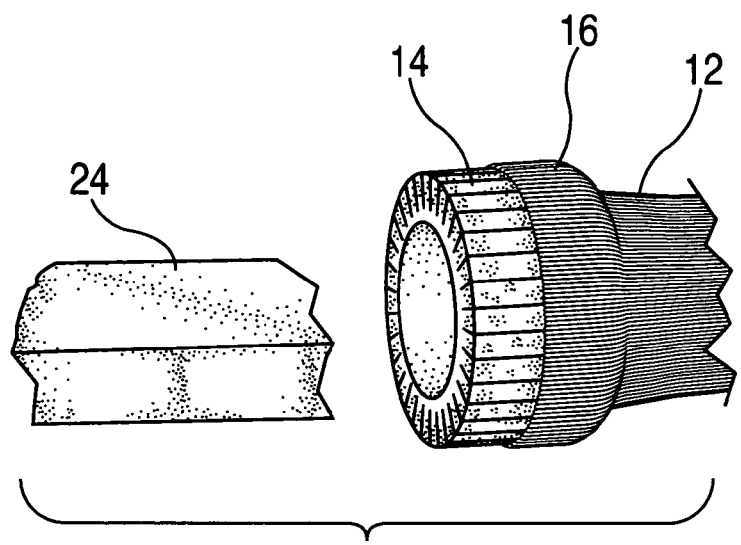
FIG. 6 is a side view of the standoff holder and a gel pad.

FIG. 6 is an image of a gel pad 24 and multi-ribbed standoff holder 10 without a transducer 20 placed with its elastic sock 12. Note that the shape of multi-ribbed standoff holder 10 now is round.

Figure 7:
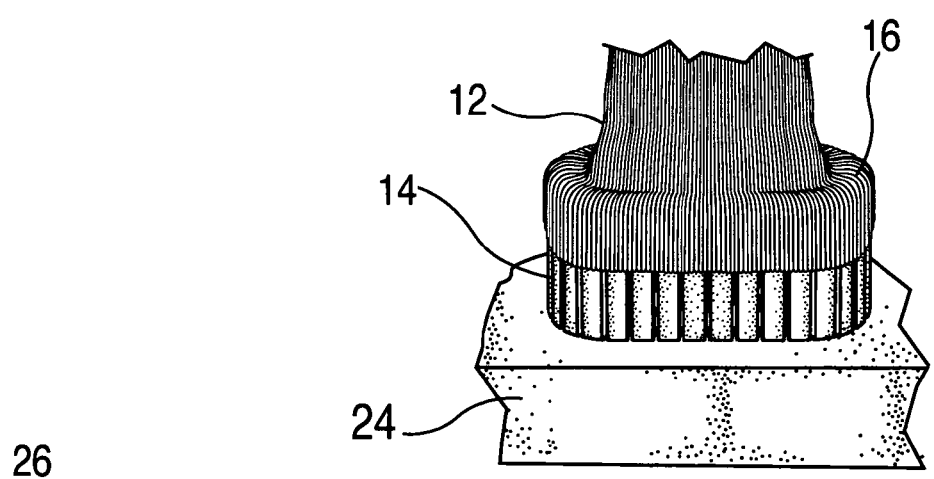
FIG. 7 is a drawing of the standoff holder place on top surface of a gel pad.

In FIG. 7 multi-ribbed standoff holder 10 has been placed over the exterior surface of ultrasound transducer 20. Multi-ribbed standoff holder 10 because of the ability of elastic sock 12 to stretch, accommodates the exterior shape of ultrasound transducer 20. When multi-ribbed standoff holder 10 is placed on the top surface of gel pad 24 as depicted in FIG. 7, an impression of the exact shape of expansion collar 14 can be made on the surface of gel pad 24.

Figure 8:
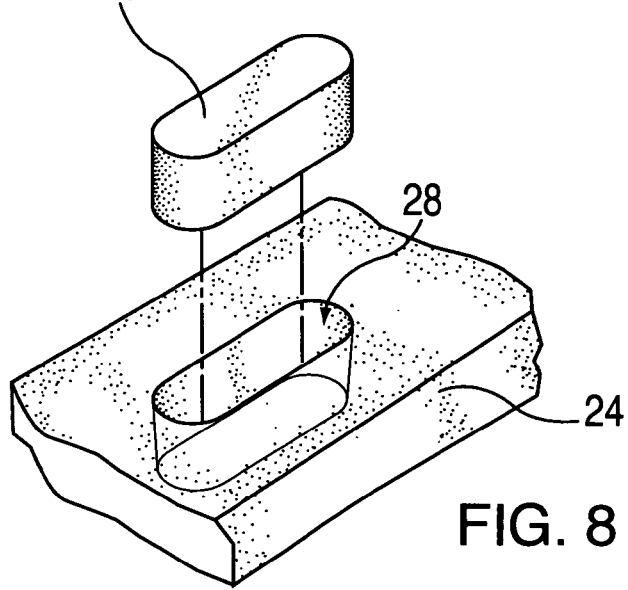
FIG. 8 is view of a gel pad with a gel insert removed from the gel pad

In FIG. 8, a drawing of a gel pad 24 having had a gel insert 26 removed. Once removed, a void 28 is produced within gel pad 24.

FIG. 9 now illustrates multi-ribbed standoff holder 10 mounted over the external surface of ultrasound transducer 20 with gel insert 26 placed within opening 18 of expansion collar 14. Gel insert 26 touches and covers acoustic window 22 located on the distal end of ultrasound transducer 20.

FIG. 10 is a cross section of multi-ribbed standoff holder 10 taken at lines 10—10 in FIG. 9. Here, one can see the relationship of the following: Observe that gel insert 26 lies directly on top of and touches the surface of acoustic window 22 on the distal end of ultrasound transducer 20. Gel insert 26 is surrounded and held in place by expansion collar 14 over the distal end of ultrasound transducer 20.

Figure 11:
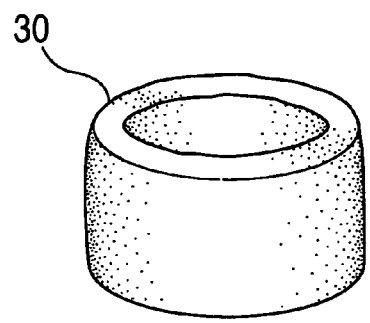
FIG. 11 is a picture of a standoff collar.
Figure 12:
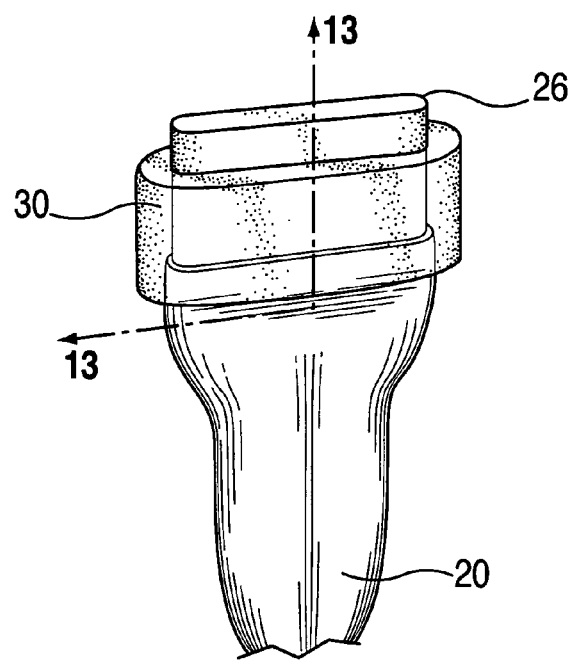
FIG. 12 is the standoff collar with gel insert placed over the end of a transducer

FIG. 11 is an elastic collar 30 that can also accommodate different shapes of transducers 20. Elastic collar 30 does not have expansion ribs 14 nor is part of an elastic sock 12. Elastic collar 30 is placed over the end of a transducer 20 as shown in FIG. 12. In FIG. 12, gel insert 26 is placed within the open end of elastic collar 30. The relationship of elastic collar 30, gel insert 26, and the distal end of transducer 20 can be visualized in FIG. 13; a cross-section that is taken at lines 13—13 in FIG. 12 thereof.

OPERATION—FIGS. 1–13

To use multi-ribbed standoff holder 10 a health care practitioner or technician will need to first mount the novel device over the exterior surface of a transducer 20.

Directing attention to FIGS. 1, 2, 3, 4, & 5. FIG. 3, is a picture of typical ultrasound transducer 20 which has incorporated on its distal end, an acoustic window 22. Transducer 20 utilizes this acoustic window 22 to transmit ultrasound waves into a body for therapeutic or diagnostic imaging purposes. For the purpose of diagnostic imaging, this same acoustic window 22 provides an avenue for resultant echoes generated by a body from ultrasound waves to pass back into the transducer 20. The echoes are then compiled into an image. To mount (FIG. 1) multi-ribbed standoff holder 10 on a typical transducer 20, an operator or technician will first grasp standoff holder 10 by elastic sock 12. Next, the technician slips the distal end of transducer 20 inside sock 12 and pulls standoff holder 10 over the body of transducer 20. Transducer 20 is pushed toward the distal end of standoff holder 10 until it is approximately 1–2 cm from the distal end of expansion collar 14. Once mounted, standoff holder 10 conforms to the shape of transducer 20 as seen in FIG. 4. Another view of transducer 20 with standoff holder 10 on its external surface can be view in FIG. 5. In this view, one is looking into the distal end of standoff holder 10. Note acoustic window 22 is fully exposed in the center of standoff holder 10. Also note that expansion slots 16 are opened between the plastic strips that make up expansion collar 14. Notice how expansion collar 14 accommodates the shape of transducer 20. In FIG. 2 expansion collar 14 appears round when not mounted over transducer 20, and oblong shaped when transducer 20 is placed within (FIG. 5).

Directing attention to FIGS. 6, 7, 8, 9, & 10. Now that multi-ribbed standoff holder 10 has been mounted over the exterior of transducer 20, a contact media will need to be place within expansion collar 14. Pad 24 may be comprised of gel or any other material that freely allows the passage of ultrasound waves and subsequent echoes from and transducer 20. FIG. 6 is comprised of two drawings; one that depicts an image of gel pad 24, the other multi-ribbed standoff holder 10 with no transducer 20. Gel pad 24 can be of any number of thicknesses. In FIG. 7, transducer 20 is now inserted inside multi-ribbed standoff holder 10. Standoff holder 10 and transducer 20 are placed directly on top of gel pad 24. A simple impression or tracing of the shape of multi-ribbed standoff holder 10 may now be made on the surface of gel pad 24. Using a knife, razor, punch, or other sharp object to cut a gel pad 24, an insert 26 can be constructed. Gel insert 26 can then be removed from gel pad 24 leaving a void 28 (FIG. 8) in gel pad 24. Gel insert 26 can now be inserted into expansion collar 14 as seen in FIG. 9. Consider too that if gel insert 26 is cut slightly larger than opening 18 within collar 14, expansion ribs 16 have the capacity to accommodate gel insert 26. FIG. 10 illustrates a sectional view of standoff holder 10, transducer 20, and gel insert 26 taken at lines 10—10 in FIG. 9. In FIG. 10, gel insert 26 is touching acoustic window 22 on the distal end of transducer 20. Gel insert 26 is not fixed to expansion collar 14. When a sonographer applies gel insert 26 against a body during an exam/treatment, gel insert 26 is free to move and presses against acoustic window 22 of transducer 20. This movement within expansion collar 14 insures contact between gel insert 16 and acoustic window 22. In addition, should a thicker gel insert 26 be necessary, a sonographer may accommodate various thicknesses of gel inserts 26 by doing the following:

1. Slide multi-ribbed standoff holder 10 distal for a thicker gel insert 26.
2. Slide multi-ribbed standoff holder 10 proximal for a thinner gel insert 26

In effect, increasing or decreasing the distance that expansion collar 14 extends past the end of transducer 20.

Figure 13:
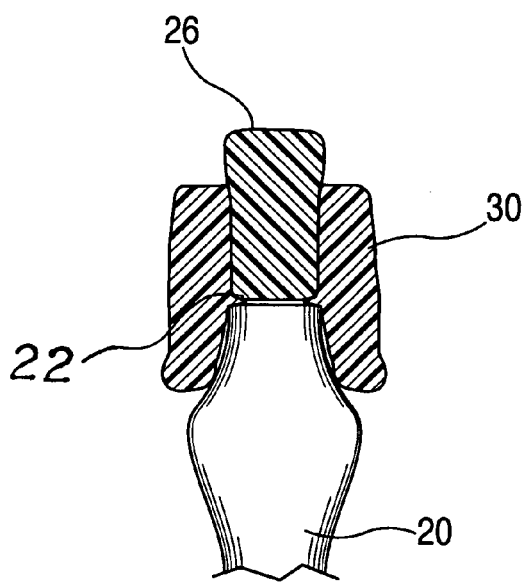
FIG. 13 is a second view of the standoff collar and gel insert taken at lines 13—13 in FIG. 12.

Directing attention to FIGS. 11, 12, & 13. FIG. 11 is a drawing of an elastic collar 30. Elastic collar 30 can be made of any number of materials that have properties like that of rubber. Elastic collar 30 lack expansion ribs 16 and elastic sock 12. Elastic collar 30 is applied to the distal end of a transducer 20. When elastic collar 30 is mounted and stretched over the end of transducer 20, (FIG. 12) elastic collar 30 changes to the shape of transducer 20. Gel insert 26 may then be constructed by tracing or making an impression of the shape of elastic collar 30 on gel pad 24. Gel insert 26 should then be cut and remove from gel pad 24 as described above paragraphs. Elastic collar 30 may accommodate a number of different sizes and shaped transducers 20. FIG. 13 is a sectional view of elastic collar 30, transducer 20, and gel insert 26 taken at lines 13—13 in FIG. 12 thereof. Gel insert 26 (FIG. 13) is free to move against the surface of transducer 20 which insures solid contact between acoustic window 22 and gel insert 26.

SUMMARY AND SCOPE

After reading the forestated description of multi-ribbed standoff holder 10, elastic collar 30, and gel insert 26 it becomes apparent that this invention will provide a healthcare practitioners with a superior means to utilize an ultrasound coupling device. This invention allows the operator of an ultrasound unit a number of options that previous devices fail to offer. The disclosed method is easy to mount onto transducer 20 and is extremely cost effective.

Also multi-ribbed standoff holder 10, elastic collar 30, and gel insert 26:

Does not require a ridge, notch, or other attachment means on a transducer 20.

Has application for both diagnostic and therapeutic ultrasound.

Reduces the risk of transmitting micro-organisms by using a disposable gel insert 26.

Eliminates any type of chambers which need to be filled with fluid and subsequently avoids air bubbles, leaks, and problems that occur with such contact media.

Has a gel insert 26 which is not fixed to a cover or incorporated into a mold. Rather, gel insert 26 is dynamic and insures total contact with acoustic window 22 when utilized.

Reduces the high cost of having to manufacture custom molded covers or custom molded silicon based standoffs.

Provides a single device which may be used on a number of different types of transducers 20 and or transducers 20 of different sizes and shapes.

Vastly improves on present methods of manufacturing standoff pads.

Stands along in its ability to provide a single high quality contact media for multiple uses and applications.

Allows the use of gel inserts 26 of a variety of materials and gel inserts 26 of different thickness.

Has application in doctors' offices, clinics, nursing homes, skilled care facilities, hospital emergency room and hospital clinics Can be used in veterinary medicine or in any application were the benefits of a standoff pad may be needed.

Finally standoff holder 10, elastic collar 30, and gel insert 26 eliminates having to use two hands while using ultrasound transducer 20 and provides comfort for those whom are receiving therapeutic ultrasound treatment or being imaged using diagnostic ultrasound.

The above description shall not be construed as limiting in ways which this many other variation by those skilled in the are who's changes or modification could be made without departing from the broad interest, intent, and true spirit of this invention.

The invention claimed is:

1. A standoff holder for an ultrasound transducer probe used in diagnostic ultrasound exams or therapeutic ultrasound treatment to insure coupling with a body comprising:
    an elongated elastic sock for mounting over said ultrasound transducer probe including an acoustic window comprising a first open end and a second open end and an internal aperture extending therethrough, wherein the cross-sectional shape of the elastic sock conforms to the shape of the ultrasound transducer probe when mounted into said standoff holder, wherein,
    said first open end includes an expansion collar including a plurality of spaced rigid strips mounted circumferentially about said ultrasound transducer probe including said acoustic window when said probe is mounted into said standoff holder.

2. A standoff holder in accordance with claim 1 wherein:
    the spaced rigid strips are separated by elastic sock forming a plurality of expansion ribs and said elastic sock comprises a series of parallel axial ribs of elastic material.

3. A standoff holder in accordance with claim 2 wherein:
    the elastic sock comprises material with decreasing flexibility and increasing rigidity from the second open end to the expansion collar at the first open end.

4. A standoff holder in accordance with claim 1 wherein:
The rigid strips in the collar comprise a spaced plurality of axial plastic strips.

5. A standoff holder in accordance with claim 1 wherein: the cross-sectional configuration of the elastic sock is round when unmounted on a probe.

6. A standoff holder in accordance with claim 1 further including:
a gel insert removably mounted and self-adjusting within the ribbed collar.

7. A standoff holder for an ultrasound transducer probe used in diagnostic ultrasound exams or therapeutic ultrasound treatment to insure coupling with a body comprising:
an elastic collar for mounting over the external surface of said ultrasound transducer probe comprising a first open end including a plurality of rigid strips and a second open end and an internal aperture extending therethrough to accommodate the shape of the ultrasound transducer probe including an acoustic window when mounted into said standoff holder, wherein, said elastic collar mounted about said ultrasound transducer probe and extending outwardly from said acoustic window; and a gel insert removably mounted and self-adjusting with said collar in engagement with said ultrasound transducer probe's acoustic window and extending outwardly therefrom.

* * * * *